United States Patent [19]

Earhart

[11] Patent Number: 4,967,919
[45] Date of Patent: Nov. 6, 1990

[54] BLOOD COLLECTION TUBE SAFETY CAP
[75] Inventor: Stephen B. Earhart, St. Louis, Mo.
[73] Assignee: Sherwood Medical Company, St. Louis, Mo.
[21] Appl. No.: 375,796
[22] Filed: Jul. 5, 1989

Related U.S. Application Data

[63] Continuation-in-part of Ser. No. 276,087, Nov. 23, 1988, abandoned.

[51] Int. Cl.⁵ ............................................. B65D 39/00
[52] U.S. Cl. ...................................................... 215/247
[58] Field of Search ........................ 215/247, 248, 249; 604/415

[56] References Cited

U.S. PATENT DOCUMENTS

| | | | |
|---|---|---|---|
| 2,388,634 | 11/1945 | DeWoody | 604/415 |
| 2,848,130 | 8/1958 | Jesnig | 215/247 X |
| 3,071,274 | 1/1963 | Ravn | 215/249 |
| 3,387,609 | 6/1968 | Shields | 215/247 X |
| 3,958,572 | 5/1976 | Lawhead | 215/247 X |
| 4,441,621 | 4/1984 | Matukura | 215/247 |
| 4,465,200 | 8/1984 | Percarpio | 215/247 |

Primary Examiner—Donald F. Norton
Attorney, Agent, or Firm—Andrew J. Beck; Montgomery W. Smith; Richard D. Allison

[57] ABSTRACT

A blood collection assembly is provided for blood collection tubes, and more particularly for evacuated blood collection tubes, whereby the potential exposure of laboratory technicians or hospital personnel to potentially infectious blood specimens is reduced. The device consists of a cap which is configured to be placed over and fitted onto the rubber stopper of an evacuated collection tube. The top surface of the cap includes a centrally located bore section which is surrounded by a downwardly directed retaining ring to prevent accidental exposure of the user to the upper flange portion of the stopper wherein the user is protected from exposure to the contaminated bottom surface of the stopper as the cap and stopper are removed from the collection tube.

17 Claims, 2 Drawing Sheets

U.S. Patent    Nov. 6, 1990    Sheet 1 of 2    4,967,919
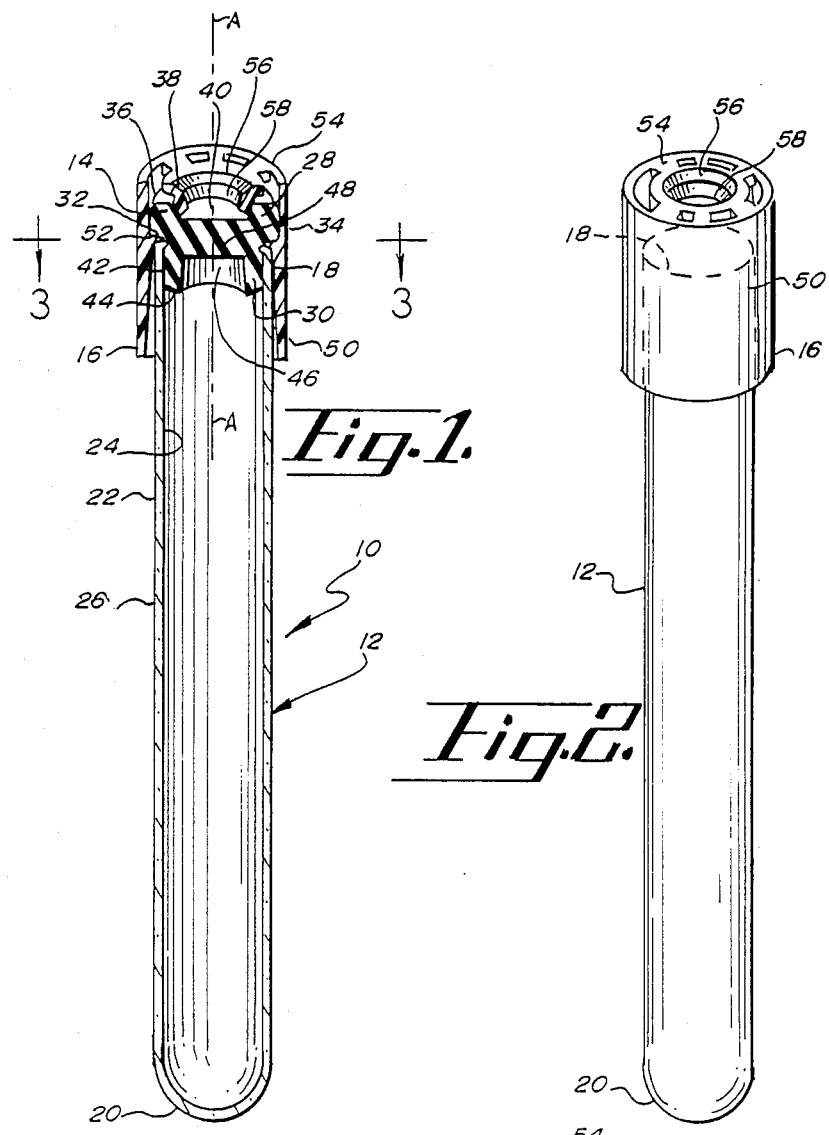
Fig.1.
Fig.2.
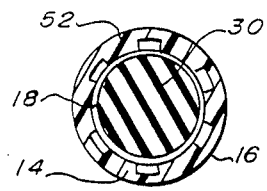
Fig.3.
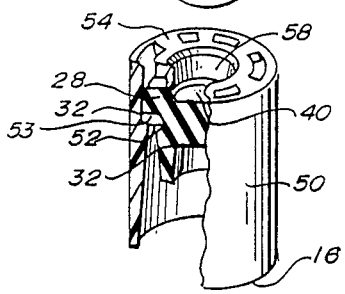
Fig.4.

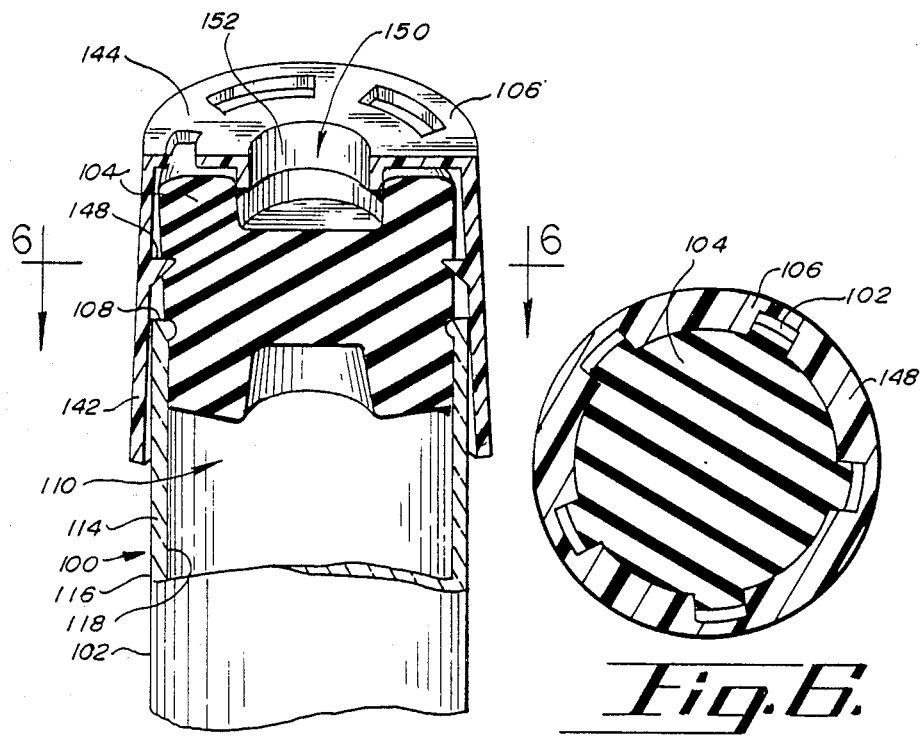
Fig.5.
Fig.6.
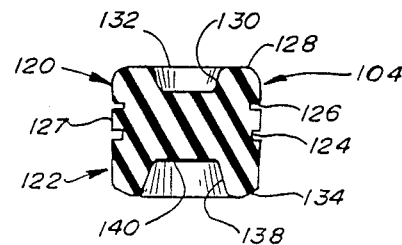
Fig.7.

BLOOD COLLECTION TUBE SAFETY CAP

This is a continuation-in-part of copending application(s) Ser. No. 07/276,087 filed on Nov. 23, 1988 now abandoned.

Field of the Invention

This invention relates generally to blood collection tubes and more particularly to a three-part blood collection assembly consisting of a collection tube, an elastomeric stopper and a protective safety cap.

Background of the Invention

The use of evacuated tubes for the collection of blood samples is well known. Conventional blood collection tubes consist of a cylindrical container or tube having a closed bottom end and an open top end. The collection tubes are then evacuated and sealed by a removable needle-pierceable stopper or closure. Typically, blood is withdrawn from a patient by first puncturing a vein with one end of a double-ended needle and then, while firmly holding the needle housing, pushing the needle-pierceable stopper of a collection tube against the other end of the needle until the stopper is pierced. The partial vacuum within the collection tube causes the blood to be drawn or siphoned into the collection tube. After the desired volume of blood is drawn into the collection tube, the needle is withdrawn from the patient and the blood specimen is brought to a laboratory for testing.

It is fairly common for laboratory technicians or hospital personnel to take several samples from a single blood specimen. Because the collection tube is originally evacuated, there is often a pressure differential between the interior and exterior of the collection tube. Therefore, when the technician removes the needle from the diaphragm of the stopper after obtaining the sample, there may be a part of the blood specimen which contacts and remains on the stopper. For other types of tests, the technician may actually remove the stopper from the blood collection tube in order to obtain the desired sample. This may expose the technician to the bottom of the stopper which has previously been contaminated with the blood specimen. Finally, when the technician reinserts the stopper into the collection tube, an aerosol of the specimen may be created around the perimeter of the stopper due to the slight positive pressure which is created within the collection tube as the stopper is reinserted into the collection tube.

The heightened awareness about the potential routes of transmission of Acquired Immune Deficiency disease and other infectious diseases has led to an increase in research relating to the development of blood collection devices which are designed to decrease the likelihood that laboratory technicians and hospital personnel will be exposed to the potentially infectious blood specimens. One such device is illustrated in U.S. Pat. No. 4,465,200, issued to Percarpio on Aug. 14, 1984. The Percarpio device consists of a standard blood collection tube and a composite closure arrangement consisting of a modified stopper and a protective cap. The Percarpio patent relies on the existence of a cavity formed by the annular portion of a cap and the inner surface of a well to protect the technician from exposure to blood droplets typically present on the top surface of the well. An important drawback to the composite closure design disclosed by Percarpio is that it requires modification of the upper flange portion of the stopper in order to create a tapered annular outer sealing surface of the type illustrated in FIG. 1. Additionally, the cap prevents the user from being able to visually determine the amount of specimen actually deposited on the flexible stopper as the needle is removed from the collection tube. As a result, the technician may be unnecessarily exposed to the potentially dangerous blood specimen present on the top surface of the stopper if the tube is shaken or inverted.

SUMMARY OF THE INVENTION

It is, therefore, an object of the present invention to provide an improved blood collection assembly which is relatively economical, simple and effective in use, and which substantially overcomes one or more of the above-identified problems.

Another object of the present invention is to provide a blood collection assembly which will decrease the likelihood that hospital personnel or laboratory technicians will be exposed to the contaminated surfaces on a stopper used in blood collection tubes.

The blood collection assembly of the present invention consists generally of a standard blood collection tube, an elastomeric stopper and a protective cap. The blood collection tube of the present invention includes an open top end and a closed bottom end. The stopper of the present invention generally includes a top surface having a top axial recess thereon and a bottom surface having a larger concave recess thereon. The stopper generally consists of an upper flange portion having a circumference larger than the open end of the collection tube and a lower plug portion having a circumference slightly larger than the inner diameter of the collection tube to create a releasable frictional fit between the lower portion of the stopper and the collection tube.

The cap of the present invention includes a lower annular portion having a plurality of inwardly extending retaining lips thereon and a top portion having a centrally located small diameter bore section surrounded by a downwardly directed retaining ring. When the cap and stopper are assembly on the collection tube, the lower annular portion extends downwardly along the outer surface of the collection tube beyond the bottom surface of the stopper. The retaining ring extends downwardly into the interior of the cap to contact the top axial recess located on the top surface of the stopper while the inwardly extending retaining lips contact an annular ridge formed by the bottom surface of the upper portion of the stopper.

A second embodiment of the present invention is illustrated in FIGS. 5-7. This embodiment is particularly adapted for use with a 16 mm or larger blood collection tubes and may be adapted for use with nearly any blood collection tube having an inwardly directed annular lip at the open end of the blood collection tube. In this embodiment, the stopper includes upper and lower groove areas wherein the lower groove area contacts the inwardly directed lip on the blood collection tube and the upper groove contacts and engages the modified inwardly directed retaining lips on the cap. The retaining ring of this embodiment is similar to the retaining ring of the first embodiment and extends downwardly into the top axial recess of the stopper to allow the user to visually determine whether or not the top surface of the stopper has been contaminated.

An advantage of the present invention is that it is relatively inexpensive to manufacture and simple to use.

A further advantage of the present invention is that the small diameter bore section and the retaining ring decrease the likelihood that the user will contact the contaminated top surface of the stopper.

A further advantage of the present invention is that the user is able to readily detect the presence of the potentially hazardous blood specimen on the top surface of the stopper.

A further advantage of the present invention is that the lower annular portion of the cap extends beyond the bottom of the stopper to decrease the likelihood that the user will contact the contaminated bottom surface of the stopper.

A further advantage of the present invention is that the stopper of the present invention may be used with a variety of clinical laboratory equipment.

A further advantage of the present invention is that the design of the stopper assists in the proper orientation of the cap on the stopper and blood collection tube.

Yet another advantage of the present invention is that the retaining lips on the cap cooperate with the bottom surface of the upper flange portion of the stopper to retain the stopper within the cap.

BRIEF DESCRIPTION OF THE DRAWINGS

FIG. 1 is a longitudinal, cross-sectional view of the blood collection assembly of the present invention;

FIG. 2 is a top plan view of the present invention;

FIG. 3 is a cross-sectional view of the present invention taken along lines 3—3 of FIG. 1;

FIG. 4 is a partial cross-sectional view of the closure assembly of the present invention;

FIG. 5 is an enlarged longitudinal, cross-sectional view of a second embodiment of the present invention;

FIG. 6 is a cross-sectional view of the second embodiment of the present invention taken along lines 6—6 of FIG. 5; and FIG. 7 is a cross-sectional view of the stopper of the second embodiment of the present invention.

DETAILED DESCRIPTION OF THE PREFERRED EMBODIMENT

The blood collection assembly of the present invention is referred to herein generally as blood collection assembly 10. The blood collection assembly 10 consists of a blood collection tube 12, an elastomeric stopper 14 and a protective cap 16. The blood collection tube 12 is typically evacuated to subsequently receive a blood specimen therein. The blood collection tube includes an open top end 18, a closed bottom end 20 and a cylindrical wall 22 having inner and outer surfaces thereon, 24 and 26, respectively.

The stopper 14 is cylindrical about a centerline or axis illustrated in FIG. 1 as reference axis A—A. The stopper 14 is preferably constructed of butyl rubber or similar elastomeric materials. The stopper 14 consists of an upper flange portion 28 and a lower plug portion 30, wherein the horizontal circumference of the upper flange portion 28 is larger than the horizontal circumference of the lower plug portion 30 and the top end 18 of the collection tube 12. An annular groove 32 circumscribes the stopper 14 along the intersection of the upper flange and lower plug portions, 28 and 30, respectively, of the stopper 14. The upper flange portion 28 of the stopper 14 consists of a generally vertical cylindrical wall 34 and a top surface 36 having a top axial recess 38 therein. The top axial recess 38 preferably tapers downwardly from the top surface 36 to a flat diaphragm surface 40 located beyond the vertical midpoint of the upper flange portion 28.

The lower plug portion 30 preferably tapers inwardly and downwardly from the annular groove 32 to form a frustoconical surface 42. A further frustoconical nose portion 44 extends inwardly and downwardly from the frustoconical surface 42 to form the bottom end of the stopper 14. A concave diaphragm surface 46 is located inwardly from the frustoconical nose portion 44 and extends upwardly approximately one-half of the length of the lower plug portion 30. A needle-pierceable diaphragm 48 is formed between the flat diaphragm surface 40 and the concave diaphragm surface 46.

The cap 16 is generally cylindrical about the centerline or axis illustrated in FIG. 1 as reference axis A—A. The cap 16 of the present invention is preferably constructed of polypropylene or another semi-rigid material. The cap 16 consists of a lower annular portion 50 having a plurality of inwardly extending retaining lips 52 thereon and a top portion 54 having a centrally located small diameter bore section 56 which is surrounded by a downwardly directed retaining ring 58.

The outer surface of the lower annular portion 50 extends downwardly and generally parallel to the outer sidewall surface 26 of the collection tube 12. In the preferred embodiment, the lower annular portion 50 includes a plurality of evenly spaced retaining lips 52 which gradually taper inwardly and upwardly along the inner surface of the lower annular portion 50. As illustrated in the drawings, the retaining lips 52 preferably extend intermittently along the inner surface of the annular portion 50.

The top portion 54 of the cap 16 is generally flat and includes a centrally 35 located small diameter bore section 56 which is in alignment with and allows access to the flat diaphragm surface 40 of the stopper 14. The retaining ring 58 surrounds the bore section 56 and extends downwardly into the interior of the cap 16 to contact the top axial recess 38 on the stopper 14.

The blood collection assembly 10 of the present invention is designed to maintain the evacuated condition of the blood collection tube 12 prior to the insertion of the blood specimen, and also to decrease the likelihood that laboratory technicians or hospital personnel will be exposed to the potentially infectious blood specimens. The stopper 11 of the present invention is designed to be inserted into the top end 18 of the blood collection tube 12 until the rim of the collection tube 12 is adjacent to the annular groove 32. The tapered frustoconical surface 42 of the lower plug portion 30 causes the stopper 14 to frictionally fit within the top end 18 of the collection tube 12. Once the stopper 14 has been inserted into the evacuated collection tube 12, the cap 16 is pressed downwardly onto the upper flange portion 28 of the stopper 14. The cap 16 is pressed downwardly over the stopper 14 until the retaining lips 52 pass over the upper flange portion 28 of the stopper 14 and become aligned generally adjacent to the annular groove 32. In this position, the retaining lips 52 contact the annular surface 53 formed by the bottom of the upper flange portion 28 of the stopper 14. Additionally, the retaining ring 58 contacts the top axial recess 38 on the stopper 14 as the top axial recess 38 tapers inwardly and downwardly to the flat diaphragm surface 40.

The cap 16 of the present invention serves two protective functions. First, when the user removes the stopper 14 and cap 16 from the blood collection tube 12, the lower plug portion 30 of the stopper 14 has a tendency to elongate slightly due to the frictional fit created between the stopper 14 and the inner sidewall surface 24 of the collection tube 12. The cap 16 of the present invention is designed to prevent the separation of the stopper 14 from the cap 16 when the stopper 14 begins to elongate. In the present invention, the resistance caused by removing the stopper 14 from the collection tube 12 causes the annular surface 53 at the bottom of the upper flange portion 28 to contact the intermittently spaced retaining lips 52.

The second function of the cap 16 is to decrease the likelihood that the user will contact the contaminated surfaces of the stopper 14. The small diameter bore section 56 and the retaining ring 58 enable the user to visually inspect the flat diaphragm surface 40 of the stopper 14 to determine whether or not the flat diaphragm surface 40 has been contaminated by the specimen. The small diameter bore section 56 and the retaining ring 58 also prevent the user from accidentally contacting the flat diaphragm surface 40 of the stopper 14 by creating a reduced diameter opening to the stopper 14 and ensuring that the flat diaphragm surface 40 is spaced below the top portion 54 of the cap 16. The lower annular portion 50 of the cap 16 extends downwardly beyond the bottom of the stopper 14 to protect against accidental contact with the contaminated bottom end of the stopper 14. Additionally, the lower annular portion 50 is designed to decrease the likelihood that the user will be exposed to the aerosol of the specimen by forming a protective ring around the top end 18 of the collection tube 12 as the stopper 14 is removed from the collection tube 12.

FIGS. 5–7 illustrate a preferred second embodiment wherein the blood collection assembly is referred to generally as blood collection assembly 100. The blood collection assembly 100 of this embodiment includes a blood collection tube 102, an elastomeric stopper 104 and a protective cap 106. The blood collection tube 102 of this embodiment is preferably a 16 mm or larger blood collection tube and includes an inwardly directed annular lip 108 on the open top end 110 thereof as compared to the cylindrical blood collection tube 12 illustrated in FIGS. 1–4 which is typically 13 mm or smaller. The blood collection tube 102 also includes a closed bottom end (not shown) and a cylindrical wall 114 having inner and outer surfaces thereon, 116 and 118, respectively. As with the first embodiment, the blood collection assembly 100 of this embodiment is typically evacuated to subsequently receive a blood specimen therein.

The stopper 104 is generally cylindrical and is preferably constructed of butyl rubber or similar elastomeric materials. The stopper 104 includes an upper flange portion 120 and a lower plug portion 122, wherein the horizontal circumference of the stopper 104 gradually increases from the lower plug portion 122 to the upper flange portion 120. A first annular groove 124 is located approximately midway along the side of the stopper 104 also includes a further second annular groove 126 spaced above the first annular groove 124 approximately midway between the first annular groove 124 and the top surface 128 along the upper flange portion 120 of the stopper 104. The upper flange portion 120 of the stopper 104 consists of a generally vertical cylindrical side surface 127 and a top surface 128 having a top axial recess 130 therein. The top axial recess 130 preferably tapers downwardly and inwardly from the top surface 128 to a flat diaphragm surface 132 located slightly beyond the second annular groove 126 at the approximate midpoint of the upper flange portion 120.

The lower plug portion 122 of the stopper 104 has an outer diameter which is slightly smaller than the outer diameter of the upper flange portion 120. The bottom surface 134 of the lower plug portion 122 tapers upwardly a slight distance from the inner surface to an outer surface adjacent to the cylindrical side surface 127 of the lower plug portion 122. The inner surface of the bottom surface 134 includes a bottom axial recess 138 which tapers upwardly and inwardly to a second generally flat diaphragm surface 140. The bottom axial recess 138 of the lower plug portion tapers inwardly more than the top axial recess 130 to form a lower opening which is slightly larger than the top opening in the stopper 104.

The cap 106 of the second embodiment is preferably constructed of a semi-rigid material such as polypropylene and consists of a generally cylindrical side surface 142, a substantially flat top surface 144 and an open bottom surface. A plurality of inwardly directed retaining lips 148 are located along the inner surface of the cap 140 approximately three fourths of the distance from the bottom surface 146 to the top surface 144 along the cylindrical side surface 142. In the present embodiment, the retaining lips 148 extend inwardly in a generally perpendicularly manner from the side surface 142 and the lower end of each retaining lip 148 tapers upwardly to form a generally flat ledge which contacts and retains the stopper 104 within the cap 140. As illustrated in the drawings, the retaining lips 148 extend intermittently along the inner surface of the side surface 142 of the cap 106.

The top surface 144 of the cap 106 is generally flat and includes a centrally located small diameter bore section 150 which is in alignment with and allows access to the flat diaphragm surface 132 of the stopper 104. A retaining ring 152 surrounds the small diameter bore section 150 and extends downwardly into the interior of the cap 106 to contact the top axial recess 130 on the stopper 104.

When the blood collection assembly 100 of the present embodiment is assembled, the stopper 104 is retained within the cap 106 by retaining the upper flange portion 120 of the stopper 104 within the upper section of the cap 106. This is accomplished by pressing the cap 106 downwardly on the stopper 104 until the retaining lips 148 on the cap 106 contact the second annular groove 126 on the stopper 104. The stopper 104 is retained on the blood collection tube 102 by the contacting relation between the first annular groove 124 on the stopper 104 and the inwardly directed annular lip 108 on the open top end 110 of the blood collection tube 102. As illustrated in FIG. 5 (and FIGS. 1 and 4), the side surface 142 of the cap 106 extends downwardly along the outer surface 116 of the cylindrical wall 114 in a generally parallel and slightly spaced apart manner. This orientation allows the stopper 104 to be removed from the open top end of the blood collection tube 102 without interference from the side surface 142 of the cap 106.

In addition to the protective functions described above, the second embodiment consistently retains the stopper 104 within the cap 106 by creating separate areas for contact between the stopper 104 and the cap 106 and the stopper 104 and the blood collection tube 102. The retaining ring 152 on the cap 140 serves to properly orient the stopper 104 within the cap 106 as the blood collection assembly 100 is assembled.

It is to be understood that various modifications may be made to the preferred embodiment without departing from the scope of the invention as defined by the attached claims. For example, it is contemplated that the retaining ring may be elongated to contact and press against the upper flange portion of the stopper to decrease the deformation of the stopper as the stopper is removed from the collection tube. Additionally, the retaining lips of the present invention may be oriented along the inner surface of the lower annular portion of the cap in a variety of shapes and sizes as long as there is sufficient contact between the annular ridge and the retaining lips to prevent the upper flange portion of the stopper from separating from the cap as the stopper is removed from the collection tube.

What is claimed is:

1. A collection assembly for receiving a blood sample therein, comprising:
   a collection tube having an open end and a closed end,
   a stopper mountable on said open end of said tube wherein said stopper includes an upper flange portion and a lower plug portion wherein the circumference of said flange portion is larger than the circumference of said plug portion,
   said flange portion having top and bottom surfaces and a top axial recess on said top surface and wherein said plug portion includes a bottom axial recess on said bottom surface to form a diaphragm between said top axial recess and said bottom axial recess,
   a cap mountable on said stopper wherein said cap includes a generally flat top surface and an open bottom end for receiving said stopper therein,
   said cap further including a lower annular portion extending downwardly from said top surface and said annular portion being spaced apart from the side of said collection tube adjacent to said bottom end of said cap,
   said top surface of said cap including a downwardly directed retaining ring, and
   said annular portion of said cap further including at least one inwardly directed retaining lip thereon, wherein said retaining ring and said retaining lip cooperate to retain said stopper within said cap and wherein said retaining ring and said top axial recess cooperate to form an open recessed area spaced downwardly from said top surface of said cap.

2. The assembly of claim 1, wherein said annular portion of said cap includes an inner surface and wherein a plurality of spaced-apart retaining lips extend inwardly from the inner surface of said annular portion to contact and retain said flange portion of said stopper within said cap.

3. The assembly of claim 2, wherein said retaining lips taper inwardly and upwardly from said bottom end of said cap to a location spaced apart from said top surface of said cap to contact an annular surface on said bottom surface of said flange portion of said stopper.

4. The assembly of claim 1, wherein the stopper is constructed of an elastomeric butyl rubber material and the cap is constructed of a semi-rigid polypropylene material.

5. The assembly of claim 1, wherein said retaining ring contacts said top axial recess on said flange portion of said stopper to form the open recessed area spaced inwardly from said retaining ring and downwardly from said top surface of said cap adjacent said top axial recess on said stopper.

6. The assembly of claim 1, wherein said stopper further includes a first annular groove between said flange portion and said plug portion and wherein said retaining lip on said cap is positioned adjacent thereto and in contacting relation with an annular surface on the bottom surface of said flange portion of said stopper.

7. The assembly of claim 1, wherein said plug portion of said stopper is frustoconically shaped and frictionally fits within said open end of said collection tube and wherein said open end of said collection tube is positioned between said plug portion of said stopper and said annular portion of said cap.

8. A collection assembly for receiving a sample of body fluid therein comprising:
   a collection tube having an open top end sidewalls and a closed bottom end,
   a stopper having an upper flange portion and a lower plug portion wherein the horizontal circumference of said flange portion is larger than the horizontal circumference of said plug portion,
   a cap having a generally flat top surface and an open bottom end for the insertion of said stopper therein,
   said top surface of said cap including an open and centrally positioned bore section surrounded by a downwardly extending retaining ring,
   a lower annular surface on said cap extending downwardly from said top surface to said bottom end of said cap in a spaced apart relation with said sidewalls of said tube,
   a retaining lip extending inwardly from said annular surface on said cap to a contacting relation with said stopper, and
   wherein said retaining ring and said retaining lip cooperate to retain said flange portion of said stopper therebetween and wherein said retaining ring and a portion of said stopper cooperate to form an open and recessed area spaced downwardly from said top surface of said cap.

9. The assembly of claim 8, wherein said top surface of said flange portion includes a top axial recess therein in alignment with said bore section of said cap and said plug portion includes an upwardly extending bottom axial recess therein to form a needle-pierceable diaphragm between said top and bottom axial recesses of said stopper.

10. The assembly of claim 8, wherein said plug portion includes a bottom axial recess on the bottom surface of said stopper and wherein the said plug portion is frustoconically shaped to allow for the frictional insertion thereof into said top end of said tube such that said sidewalls of said tube are positioned between said plug portion of said stopper and said annular surface on said cap.

11. The assembly of claim 8, wherein said flange portion of said stopper includes a bottom annular surface thereon for contacting an engagement lip on said top end of said tube to retain said stopper on said collection tube.

12. The assembly of claim 8, wherein said stopper includes an annular groove thereon for contacting said retaining lip on said cap to retain said cap on said stopper.

13. The assembly of claim 8, wherein said stopper includes first and second annular grooves thereon for retaining said cap on said stopper and retaining said stopper on said collection tube.

14. A collection assembly for receiving a sample of body fluid therein comprising;
   a collection tube having a closed bottom end, sidewalls and an open top end having an engagement lip adjacent said top end,
   a stopper having an upper flange portion and a lower plug portion and having a plurality of axial recesses on said stopper,
   a cap having a retaining lip thereon and a generally flat top surface and an open bottom end for the insertion of said stopper into said bottom end of said cap, and
   said stopper having a pair of spaced apart first and second annular grooves thereon for contacting engagement between said first annular groove and said engagement lip on said collection tube and between said second annular groove and said retaining lip on said cap to retain said cap and stopper on said collection tube.

15. The assembly of claim 14, wherein said top surface of said cap includes a centrally positioned and downwardly extending retaining ring thereon to contact said flange portion of said stopper to form an open and recessed area spaced downwardly from said top surface of said cap.

16. The assembly of claim 14, wherein said pair of spaced apart first and second annular grooves includes said annular groove on said flange portion of said stopper and wherein said second annular groove is in contacting engagement with said retaining lip on said cap to retain said stopper in said cap.

17. The assembly of claim 14, wherein said top surface of said cap includes a centrally positioned and open bore section surrounded by a downwardly extending retaining ring and wherein said retaining ring extends into one of said axial recesses on said stopper to form a recessed area spaced downwardly from said top surface of said cap.

* * * * *